(12) United States Patent
Horie

(10) Patent No.: US 12,245,856 B2
(45) Date of Patent: Mar. 11, 2025

(54) PULSE PHOTOMETER, PULSE PHOTOMETRY SYSTEM AND COMPUTER-READABLE MEDIUM

(71) Applicant: NIHON KOHDEN CORPORATION, Tokyo (JP)

(72) Inventor: Katsuyuki Horie, Tokorozawa (JP)

(73) Assignee: NIHON KOHDEN CORPORATION, Tokyo (JP)

( * ) Notice: Subject to any disclaimer, the term of this patent is extended or adjusted under 35 U.S.C. 154(b) by 424 days.

(21) Appl. No.: 17/321,682

(22) Filed: May 17, 2021

(65) Prior Publication Data

US 2021/0361202 A1 Nov. 25, 2021

(30) Foreign Application Priority Data

May 20, 2020 (JP) ................................ 2020-088252

(51) Int. Cl.
*A61B 5/1455* (2006.01)
(52) U.S. Cl.
CPC ................................ *A61B 5/14552* (2013.01)
(58) Field of Classification Search
CPC ........................... A61B 5/1455; A61B 5/14552
See application file for complete search history.

(56) References Cited

U.S. PATENT DOCUMENTS

| | | | |
|---|---|---|---|
| 7,774,037 B2 * | 8/2010 | Parker | A61B 5/14532 600/323 |
| 2004/0267140 A1 | 12/2004 | Ito et al. | |
| 2008/0221463 A1 | 9/2008 | Baker | |
| 2016/0256089 A1 | 9/2016 | Ueda et al. | |
| 2018/0168492 A1 | 6/2018 | Vermeulen | |

FOREIGN PATENT DOCUMENTS

| | | |
|---|---|---|
| JP | 4196209 B2 | 12/2008 |
| JP | 2010-082246 A | 4/2010 |
| JP | 2016-165447 A | 9/2016 |
| JP | 2018-519889 A | 7/2018 |

OTHER PUBLICATIONS

Search Report issued Oct. 29, 2021 by the European Patent Office in counterpart European Patent Application No. 21173560.0.
Office Action dated Oct. 10, 2023, issued by Japanese Patent Office in Japanese Patent Application No. 2020-088252.

* cited by examiner

*Primary Examiner* — Marjan Fardanesh
(74) *Attorney, Agent, or Firm* — Sughrue Mion, PLLC

(57) ABSTRACT

A pulse photometer includes: an interface receiving a first signal and a second signal; and a processor configured to calculate a concentration of at least one blood light absorber in the subject, based on the first and second signals. The processor is configured to: acquire a first variation of the first light due to blood pulsation in the subject, acquire a second variation of the second light due to the pulsation, and calculate the concentration of the at least one blood light absorber, based on a first correction amount and a second correction amount. The first correction amount is based on at least one of a first constant, the first variation and the second variation, which are statistically determined. The second correction amount is based on at least one of a second constant, the first variation and the second variation, which are statistically determined.

10 Claims, 1 Drawing Sheet

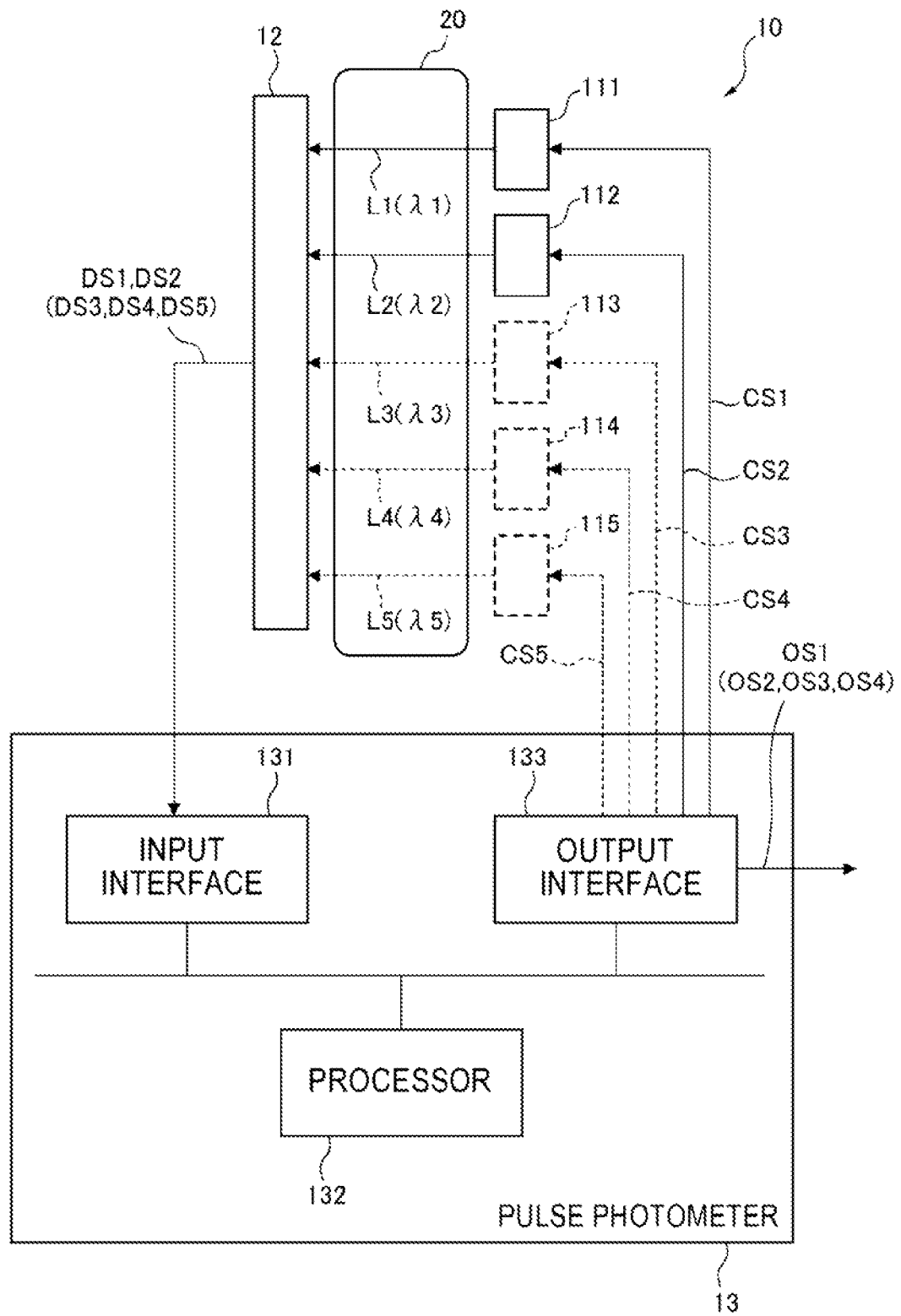

PULSE PHOTOMETER, PULSE PHOTOMETRY SYSTEM AND COMPUTER-READABLE MEDIUM

CROSS-REFERENCE TO RELATED APPLICATIONS

This application is based on and claims priority under 35 USC 119 from Japanese Patent Application No. 2020-088252 filed on May 20, 2020, the contents of which are incorporated herein by reference.

BACKGROUND

The presently disclosed subject matter relates to a pulse photometer configured to calculate a concentration of a blood light absorber in a subject. The presently disclosed subject matter also relates to a pulse photometry system including the pulse photometer, and a computer-readable medium storing a computer program that can be executed by one or more processors of the pulse photometer.

A pulse photometry system disclosed in Japanese Patent No. 4,196,209 includes a pulse photometer configured to calculate a concentration of a blood light absorber in a subject, an emitter, and a detector. The emitter is configured to irradiate a body of the subject with lights including a plurality of wavelengths where calculated extinction coefficients of the blood light absorber are different. The light passing through the body is incident on the detector. The detector is configured to output a signal corresponding to an intensity of the light of each wavelength.

The intensity of the light of each wavelength in the detector varies according to blood pulsation in the subject. The variation over time of the intensity of the light of a specific wavelength due to the pulsation is acquired as a pulse wave signal associated with the light of the wavelength.

An amplitude of the pulse wave signal associated with the light of the specific wavelength corresponds to a variation of absorbance at the time when the light of the wavelength passes through the body. The concentration of the blood light absorber is calculated based on a ratio of variations of absorbance obtained for the lights of the plurality of wavelengths.

The presently disclosed subject matter is provided to enhance calculation accuracy of a concentration of a blood light absorber in a subject.

SUMMARY

According to a first aspect of the presently disclosed subject matter, a pulse photometer includes: an input interface configured to receive a first signal, which corresponds to an intensity of a first light including a first wavelength passing through a body of a subject, and a second signal, which corresponds to an intensity of a second light including a second wavelength passing through the body; and one or more processors configured to calculate a concentration of at least one blood light absorber in the subject, based on the first signal and the second signal. The one or more processors are configured to: acquire a first variation corresponding to a variation of the first light due to blood pulsation in the subject, acquire a second variation corresponding to a variation of the second light due to the pulsation, and calculate the concentration of the at least one blood light absorber, based on a value obtained by adding a first correction amount to the first variation and a value obtained by adding a second correction amount to the second variation. The first correction amount is based on at least one of a first constant, a function of the first variation and a function of the second variation, which are statistically determined, and the second correction amount is based on at least one of a second constant, the function of the first variation and the function of the second variation, which are statistically determined According to a second aspect of the presently disclosed subject matter, a pulse photometry system includes: a first emitter configured to emit a first light including a first wavelength; a second emitter configured to emit a second light including a second wavelength; a detector configured to output a first signal, which corresponds to an intensity of the first light passing through a body of a subject, and a second signal, which corresponds to an intensity of the second light passing through the body; and one or more processors configured to calculate a concentration of at least one blood light absorber in the subject, based on the first signal and the second signal. The one or more processors are configured to: acquire a first variation corresponding to a variation of the first light due to blood pulsation in the subject, acquire a second variation corresponding to a variation of the second light due to the pulsation, and calculate the concentration of the at least one blood light absorber, based on a value obtained by adding a first correction amount to the first variation and a value obtained by adding a second correction amount to the second variation. The first correction amount is based on at least one of a first constant, a function of the first variation and a function of the second variation, which are statistically determined, and the second correction amount is based on at least one of a second constant, the function of the first variation and the function of the second variation, which are statistically determined.

According to a third aspect of the presently disclosed subject matter, a non-transitory computer-readable medium stores a computer program capable of being executed by one or more processors of a pulse photometer. When executed, the computer program causes the pulse photometer to: receive a first signal, which corresponds to an intensity of a first light including a first wavelength passing through a body of a subject; receive a second signal, which corresponds to an intensity of a second light including a second wavelength passing through the body; acquire a first variation corresponding to a variation of the first light due to blood pulsation in the subject, acquire a second variation corresponding to a variation of the second light due to the pulsation, and calculate the concentration of the at least one blood light absorber in the subject, based on a value obtained by adding a first correction amount to the first variation and a value obtained by adding a second correction amount to the second variation. The first correction amount is based on at least one of a first constant, a function of the first variation and a function of the second variation, which are statistically determined, and the second correction amount is based on at least one of a second constant, the function of the first variation and the function of the second variation, which are statistically determined.

BRIEF DESCRIPTION OF DRAWINGS

Exemplary embodiments of the presently disclosed subject matter will be described in detail based on the following figures, in which:

FIGURE is a diagram exemplifying a configuration of a pulse photometry system in accordance with an embodiment.

DESCRIPTION OF EMBODIMENTS

Hereinafter, an example of an embodiment will be described in detail with reference to the attached drawings.

FIGURE exemplifies a configuration of a pulse photometry system 10 in accordance with an embodiment. The pulse photometry system 10 may include a first emitter 111, a second emitter 112, a detector 12, and a pulse photometer 13.

The first emitter 111 may be configured to emit a first light L1 including a first wavelength $\lambda 1$. The first emitter 111 may be configured to include a light-emitting element configured to emit a light including the first wavelength $\lambda 1$, or may also be configured so that the light of the first wavelength $\lambda 1$ is emitted by enabling a light of a wavelength, which is different from the first wavelength $\lambda 1$, emitted from the light-emitting element to pass through an appropriate optical element. Examples of the light-emitting element include a light-emitting diode (LED), a laser diode (LD), an EL element and the like.

The second emitter 112 may be configured to emit a second light L2 including a second wavelength $\lambda 2$. The second wavelength $\lambda 2$ is different from the first wavelength $\lambda 1$. The second emitter 112 may be configured to include a light-emitting element configured to emit a light including the second wavelength $\lambda 2$, or may also be configured so that the light of the second wavelength $\lambda 2$ is emitted by enabling a light of a wavelength, which is different from the second wavelength $\lambda 2$, emitted from the light-emitting element to pass through an appropriate optical element. Examples of the light-emitting element include a light-emitting diode (LED), a laser diode (LD), an EL element and the like.

The detector 12 may be configured to include a light-detecting element configured to output a detection signal corresponding to an intensity of an incident light. The detection signal may be an analog signal or a digital signal. Examples of the light-detecting element include a photo diode, a photo transistor, a photo resistor and the like having sensitivity to at least the first wavelength $\lambda 1$ and the second wavelength $\lambda 2$.

The first emitter 111, the second emitter 112, and the detector 12 are configured to be attached to a body 20 of a subject. The first light L1 emitted from the first emitter 111 and the second light L2 emitted from the second emitter 112 pass through the body 20 and are incident on the detector 12. In the present example, the first emitter 111 and the second emitter 112 are arranged to face the detector 12 with the body 20 being sandwiched therebetween, so that the first light L1 and the second light L2 passing through the body 20 are incident on the detector 12. The detector 12 may also be arranged adjacent to the first emitter 111 and the second emitter 112 without the body 20 being sandwiched therebetween. In this case, the first light L1 and the second light L2 reflected on the body 20 are incident on the detector 12.

The pulse photometer 13 may include an input interface 131, one or more processors 132, and an output interface 133.

The input interface 131 may be configured to detect a detection signal output from the detector 12. When the detection signal output from the detector 12 is an analog signal, the input interface 131 may include an appropriate conversion circuit including an A/D converter.

One or more processors 132 are configured to cause the first emitter 111 and the second emitter 112 to emit the first light L1 and the second light L2. Specifically, a first control signal CS1 for causing the first emitter 111 to emit the first light L1 and a second control signal CS2 for causing the second emitter 112 to emit the second light L2 are output from the output interface 133. The first control signal CS1 and the second control signal CS2 may be analog signals or digital signals. When the first control signal CS1 and the second control signal CS2 are analog signals, the output interface 133 may include an appropriate conversion circuit including a D/A converter.

Thereby, the first light L1 and the second light L2 passing through the body 20 are incident on the detector 12. The detector 12 may be configured to output, as the detection signal, a first detection signal DS1 corresponding to an incident intensity of the first light L1 and a second detection signal DS2 corresponding to an incident intensity of the second light. The first detection signal DS1 is an example of the first signal. The second detection signal DS2 is an example of the second signal.

The input interface 131 of the pulse photometer 13 may be configured to receive the first detection signal DS1 and the second detection signal DS2. The one or more processors 132 of the pulse photometer 13 are configured to calculate a first blood light absorber concentration $\Phi 1$ in the body 20 (namely, a concentration of a first blood light absorber in the body 20) of the subject, based on the first detection signal DS1 and the second detection signal DS2. Examples of the first blood light absorber include oxyhemoglobin (O2Hb), deoxyhemoglobin (RHb), carboxyhemoglobin (COHb), methemoglobin (MetHb), and the like.

The first light L1 emitted from the first emitter 111 is absorbed by the arterial blood, the venous blood, tissues, and the like when passing through the body 20 of the subject. Therefore, the intensity of the first light L1 incident on the detector 12 is reduced as compared to the intensity upon emission from the first emitter 111. That is, as a ratio of the emission intensity from the first emitter 111 and the incident intensity on the detector 12, an absorbance A1 of the first light L1 can be defined.

Same or similarly, the second light L2 emitted from the second emitter 112 is absorbed by the arterial blood, the venous blood, tissues, and the like when passing through the body 20 of the subject. Therefore, the intensity of the second light L2 incident on the detector 12 is reduced as compared to the intensity upon emission from the second emitter 112. That is, as a ratio of the emission intensity from the second emitter 112 and the incident intensity on the detector 12, an absorbance A2 of the second light L2 can be defined.

The arterial vessel pulsates with the heartbeat of the subject, so that a thickness of the arterial vessel through which the first light L1 and the second light L2 pass varies. In other words, an amount of the arterial blood that absorbs the first light L1 and the second light L2 varies. Therefore, the intensity of the first light L1 and the intensity of the second light L2 incident on the detector 12 vary due to the blood pulsation in the subject, so that the absorbance A1 of the first light L1 and the absorbance A2 of the second light L2 vary. Variations of absorbance are defined as a first variation $\Delta A1$ and a second variation $\Delta A2$ respectively.

The first blood light absorber has a wavelength dependency on the absorbance. The first wavelength $\lambda 1$ and the second wavelength $\lambda 2$ are selected as two wavelengths that show a significant difference in absorbance. It is known that the first blood light absorber concentration $\Phi 1$ can be calculated based on a ratio $(\Delta A1/\Delta A2)$ of the first variation $\Delta A1$ and the second variation $\Delta A2$.

As described above, the first light L1 and the second light L2 are absorbed not only by the arterial blood but also the venous blood and tissues. Therefore, the first blood light absorber concentration $\Phi 1$ to be calculated is an approximate value based on assumption that the absorption by the light absorber in the arterial blood is significantly greater than the absorption by the venous blood and tissues. In other words, there is room for improvement on calculation accuracy of the blood light absorber concentration by considering the light absorption by the venous blood and tissues.

For example, if it is assumed that a distance between the detector 12 and each of the first emitter 111 and the second emitter 112 is left unchanged, when the thickness of the arterial vessel increases with the pulsation, the thickness of at least one of the venous vessel and tissues decreases, and vice versa. However, the degree and extent of the effect on the venous vessel and tissues due to the change in thickness of the arterial vessel are different for each person. This individual difference may be one of error factors of measurement by the pulse photometry. By reducing the error, it is possible to improve the calculation accuracy of the blood light absorber concentration.

In the present embodiment, the one or more processors 132 are configured to calculate the first blood light absorber concentration $\Phi 1$, based on a ratio of a value obtained by adding a first correction amount $\alpha 1$ to the first variation $\Delta A1$ and a value obtained by adding a second correction amount $\alpha 2$ to the second variation $\Delta A2$. That is, a following equation is presented.

$$\Phi 1 = (\Delta A1 + \alpha 1)/(\Delta A2 + \alpha 2)$$

Here, the first correction amount $\alpha 1$ and the second correction amount $\alpha 2$ are expressed by following equations.

$$\alpha 1 = a1 + a2 \cdot f(\Delta A1) + a3 \cdot f(\Delta A2)$$

$$\alpha 2 = b1 + b2 \cdot f(\Delta A1) + b3 \cdot f(\Delta A2)$$

Here, a1, a2, a3, b1, b2, and b3 are constants. Each of a1, a2, a3, b1, b2, and b3 may be 0 (zero). However, a case where a1, a2, a3, b1, b2, and b3 are all 0 at the same time is excluded. $f(\Delta A1)$ is an $n^{th}$-order function of the first variation $\Delta A1$ (n: an integer of 1 or greater). The function $f(\Delta A1)$ included in the first correction amount $\alpha 1$ and the function $f(\Delta A1)$ included in the second correction amount $\alpha 2$ may be the same or different from each other. $f(\Delta A2)$ is an $n^{th}$-order function of the second variation $\Delta A2$ (n: an integer of 1 or greater). The function $f(\Delta A2)$ included in the first correction amount $\alpha 1$ and the function $f(\Delta A2)$ included in the second correction amount $\alpha 2$ may be the same or different from each other.

Each constant and each function are statistically determined so as to reduce the error caused due to the individual difference, based on test data and clinical data obtained from a plurality of subjects for the first blood light absorber concentration $\Phi 1$.

In a case where the constant a2 and the constant a3 are 0, the first correction amount $\alpha 1$ is become a constant term. In this case, the constant a1 is an example of the first constant. In a case where the constant b2 and the constant b3 are 0, the second correction amount $\alpha 2$ becomes a constant term. In this case, the constant b1 is an example of the second constant. In a case where at least one of the first correction amount $\alpha 1$ and the second correction amount $\alpha 2$ is a constant term, it is possible to suppress an increase in calculation load of the one or more processors 132 for calculation of the concentration $\Phi 1$.

In a case where at least one of the constant a2, the constant a3, the constant b2 and the constant b3 has a value, at least one of the first correction amount $\alpha 1$ and the second correction amount $\alpha 2$ becomes a variable in which the light intensity of the first light L1 and the light intensity of the second light L2, which are actually incident on the detector 12, are reflected. In this case, it is possible to further reduce the error due to the individual difference for the subject to be used for calculation of the concentration $\Phi 1$.

Depending on types of the blood light absorber to be used for calculation, it is possible to calculate two blood light absorber concentrations (or saturations) by using the first light L1 and the second light L2. For example, in a case where it is assumed that there is no abnormal hemoglobin such as carboxyhemoglobin, methemoglobin and the like in hemoglobin in the arterial blood, it is possible to specify a concentration of deoxyhemoglobin by specifying a concentration of oxyhemoglobin, and vice versa. That is, in a case where it can be assumed that there are two types of light absorbers in the blood system, when a concentration of one type is specified, a concentration of the other type can be specified. As another example, a relationship between a concentration of total hemoglobin and a concentration of water in blood may be exemplified.

Therefore, the one or more processors 132 can calculate at least one blood light absorber concentration, based on a value obtained by adding the first correction amount $\alpha 1$ to the first variation $\Delta A1$ and a value obtained by adding the second correction amount $\alpha 2$ to the second variation $\Delta A2$. The first correction amount $\alpha 1$ is based on at least one of the constant a1, the function $f(\Delta A1)$ of the first variation and the function $f(\Delta A2)$ of the second variation, which are statistically determined. The second correction amount $\alpha 2$ is based on at least one of the constant b1, the function $f(\Delta A1)$ of the first variation and the function $f(\Delta A2)$ of the second variation, which are statistically determined.

As exemplified in FIGURE, the one or more processors 132 are configured to output a first output signal OS1 corresponding to the first blood light absorber concentration $\Phi 1$ from the output interface 133. The first output signal OS1 is provided to appropriate processing. Examples of the appropriate processing include calculation of a value that can be acquired based on the concentration $\Phi 1$, display of at least one of a value of the concentration $\Phi 1$ and a value acquired based on the concentration $\Phi 1$, a notification operation based on at least one of a value of the concentration $\Phi 1$ and a value acquired based on the concentration $\Phi 1$, and the like.

As exemplified in FIGURE, the pulse photometry system 10 may include a third emitter 113.

The third emitter 113 is configured to emit a third light L3 including a third wavelength $\lambda 3$. The third wavelength $\lambda 3$ is different from the first wavelength $\lambda 1$ and the second wavelength $\lambda 2$. The third emitter 113 may also be configured to include a light-emitting element configured to emit a light including the third wavelength $\lambda 3$ or may also be configured so that the light of the third wavelength $\lambda 3$ is emitted by enabling a light of a wavelength, which is different from the third wavelength $\lambda 3$, emitted from the light-emitting element to pass through an appropriate optical element. Examples of the light-emitting element include a light-emitting diode (LED), a laser diode (LD), an EL element and the like.

In this case, the detector 12 is required to have a light-receiving element having sensitivity to the third wavelength $\lambda 3$.

The third emitter 113 is configured to be attached to the body 20 of the subject. In the present example, the third emitter 113 is arranged so that the third light L3 passes through the body 20 and is then incident on the detector 12.

The third emitter 113 may also be arranged so that the third light L3 is reflected on the body 20 and is then incident on the detector 12.

In this case, the one or more processors 132 are configured to cause the third emitter 113 to emit the third light L3. Specifically, a third control signal CS3 for causing the third emitter 113 to emit the third light L3 is output from the output interface 133 at a timing different from the first control signal CS1 and the second control signal CS2. The third control signal CS3 may be an analog signal or a digital signal.

When the third light L3 passing through the body 20 is incident on the detector 12, the detector 12 outputs a third detection signal DS3 corresponding to an incident intensity of the third light L3. The third detection signal DS3 is an example of the third signal.

The input interface 131 of the pulse photometer 13 is configured to receive the third detection signal DS3, in addition to the first detection signal DS1 and the second detection signal DS2. The one or more processors 132 of the pulse photometer 13 are configured to calculate at least one blood light absorber concentration in the body 20 of the subject, based on the first detection signal DS1, the second detection signal DS2, and the third detection signal DS3.

Same or similarly to the first light L1 and the second light L2, an absorbance A3 of the third light L3 can also be defined. In addition, a third variation $\Delta A3$ corresponding to a variation of the absorbance A3 due to blood pulsation of the subject can be defined.

In the present example, the first correction amount $\alpha 1$ and the second correction amount $\alpha 2$ that are used so as to calculate the first blood light absorber concentration $\Phi 1$ are expressed as follows.

$$\alpha 1 = a1 + a2 \cdot f(\Delta A1) + a3 \cdot f(\Delta A2) + a4 \cdot f(\Delta A3)$$

$$\alpha 2 = b1 + b2 \cdot f(\Delta A1) + b3 \cdot f(\Delta A2) + b4 \cdot f(\Delta A3)$$

Here, a4 and b4 are constants. Each of a4 and b4 may be 0 (zero). However, a case where the constants a1 to a4 and the constants b1 to b4 are all 0 at the same time is excluded. $f(\Delta A3)$ is an $n^{th}$-order function of the third variation $\Delta A3$ (n: an integer of 1 or greater). The function $f(\Delta A3)$ included in the first correction amount $\alpha 1$ and the function $f(\Delta A3)$ included in the second correction amount $\alpha 2$ may be the same or different from each other.

In addition, it is possible to individually calculate a second blood light absorber concentration $\Phi 2$ (namely, a concentration of a second blood light absorber) by using the third light L3. For example, a concentration of oxyhemoglobin and a concentration of carboxyhemoglobin in the arterial blood can be individually calculated. Specifically, the one or more processors 132 are configured to calculate a second blood light absorber concentration $\Phi 2$, based on a ratio of a value obtained by adding a third correction amount $\alpha 3$ to the third variation $\Delta A3$ and a value obtained by adding the first correction amount $\alpha 1$ to the first variation $\Delta A1$ or a value obtained by adding the second correction amount $\alpha 2$ to the second variation $\Delta A2$. That is, a following equation is presented.

$$\Phi 2 = (\Delta A1 + \alpha 1)/(\Delta A3 + \alpha 3); \text{ or}$$

$$\Phi 2 = (\Delta A2 + \alpha 2)/(\Delta A3 + \alpha 3)$$

Here, the third correction amount $\alpha 3$ is expressed by a following equation.

$$\alpha 3 = c1 + c2 \cdot f(\Delta A1) + c3 \cdot f(\Delta A2) + c4 \cdot f(\Delta A3)$$

Here, c1, c2, c3, and c4 are constants. Each of c1, c2, c3 and c4 may be 0 (zero). However, a case where the constants c1 to c4 and the constants a1 to a4 or the constants b1 to b4 are all 0 at the same time is excluded. The function $f(\Delta A1)$, the function $f(\Delta A2)$, and the function $f(\Delta A3)$ included in the third correction amount $\alpha 3$ may be each the same as or different from the function $f(\Delta A1)$, the function $f(\Delta A2)$, and the function $f(\Delta A3)$ included in each of the first correction amount $\alpha 1$ and the second correction amount $\alpha 2$.

In a case where the constant c2, the constant c3 and the constant c4 are 0, the third correction amount $\alpha 3$ becomes a constant term. In this case, the constant c1 is an example of the third constant.

That is, the third wavelength $\lambda 3$ is selected as a wavelength that shows a significant difference in the absorbance of the second blood light absorber with respect to the first wavelength $\lambda 1$ or the second wavelength $\lambda 2$. Each constant and each function relating to the third variation $\Delta A3$ are statistically determined so as to suppress the effect of the individual difference with respect to the light absorption of the venous blood and tissues, based on test data and clinical data obtained from a plurality of subjects for the second blood light absorber concentration $\Phi 2$.

The one or more processors 132 are configured to output a second output signal OS2 corresponding to the second blood light absorber concentration $\Phi 2$ from the output interface 133. The second output signal OS2 is provided to appropriate processing. Examples of the appropriate processing include calculation of a value that can be acquired based on the concentration $\Phi 2$, display of at least one of a value of the concentration $\Phi 2$ and a value acquired based on the concentration $\Phi 2$, a notification operation based on at least one of a value of the concentration $\Phi 2$ and a value acquired based on the concentration $\Phi 2$, and the like.

According to the above configuration, the calculation accuracy of the second blood light absorber concentration $\Phi 2$ can also be enhanced, based on the principle described with respect to the calculation of the first blood light absorber concentration $\Phi 1$.

Note that, in a case where three different wavelengths are used, it is not necessarily required to output calculation results of a plurality of blood light absorber concentrations. In the present example, only one calculation result of the first blood light absorber concentration $\Phi 1$ and the second blood light absorber concentration $\Phi 2$ may be output. Also in this case, it is possible to enhance the calculation accuracy of each concentration, as compared to the case where the two wavelengths are used.

The concentrations of each of the plurality of light absorbers included in the blood not only increase or decrease individually but also influence each other. For example, the increase or decrease in the second blood light absorber concentration $\Phi 2$ may affect the increase or decrease in the first blood light absorber concentration $\Phi 1$. The equation for calculating the first blood light absorber concentration $\Phi 1$ by using the first light L1 and the second light L2 includes, in the correction term, the information about the third light L3 that is used so as to calculate the second blood light absorber concentration $\Phi 2$. Therefore, when calculating the first blood light absorber concentration $\Phi 1$, the effect of the second blood light absorber concentration $\Phi 2$ can be taken into consideration. Thereby, it is possible to enhance the calculation accuracy of the first blood light absorber concentration $\Phi 1$. The same also applies to the second blood light absorber concentration $\Phi 2$.

As exemplified in FIGURE, the pulse photometry system 10 may include a fourth emitter 114.

The fourth emitter 114 is configured to emit a fourth light L4 including a fourth wavelength $\lambda4$. The fourth wavelength $\lambda4$ is different from the first wavelength $\lambda1$, the second wavelength $\lambda2$, and the third wavelength $\lambda3$. The fourth emitter 114 may also be configured to include a light-emitting element configured to emit a light including the fourth wavelength $\lambda4$ or may also be configured so that the light of the fourth wavelength $\lambda4$ is emitted by enabling a light of a wavelength, which is different from the fourth wavelength $\lambda4$, emitted from the light-emitting element to pass through an appropriate optical element. Examples of the light-emitting element include a light-emitting diode (LED), a laser diode (LD), an EL element and the like.

In this case, the detector 12 is required to have a light-receiving element having sensitivity to the fourth wavelength $\lambda4$.

The fourth emitter 114 is configured to be attached to the body 20 of the subject. In the present example, the fourth emitter 114 is arranged so that the fourth light L4 passes through the body 20 and is then incident on the detector 12. The fourth emitter 114 may also be arranged so that the fourth light L4 is reflected on the body 20 and is then incident on the detector 12.

In this case, the one or more processors 132 are configured to cause the fourth emitter 114 to emit the fourth light L4. Specifically, a fourth control signal CS4 for causing the fourth emitter 114 to emit the fourth light L4 is output from the output interface 133 at a timing different from the first control signal CS1, the second control signal CS2, and the third control signal CS3. The fourth control signal CS4 may be an analog signal or a digital signal.

When the fourth light L4 passing through the body 20 is incident on the detector 12, the detector 12 outputs a fourth detection signal DS4 corresponding to an incident intensity of the fourth light L4. The fourth detection signal DS4 is an example of the fourth signal.

The input interface 131 of the pulse photometer 13 is configured to receive the fourth detection signal DS4, in addition to the first detection signal DS1, the second detection signal DS2, and the third detection signal DS3. The one or more processors 132 of the pulse photometer 13 are configured to calculate at least one blood light absorber concentration in the body 20 of the subject, based on the first detection signal DS1, the second detection signal DS2, the third detection signal DS3, and the fourth detection signal DS4.

Same or similarly to the first light L1, the second light L2, and the third light L3, an absorbance A4 of the fourth light L4 can also be defined. In addition, a fourth variation $\Delta A4$ corresponding to a variation of the absorbance A4 due to blood pulsation of the subject can be defined.

In the present example, the first correction amount $\alpha1$ and the second correction amount $\alpha2$ that are used so as to calculate the first blood light absorber concentration $\Phi1$ are expressed as follows.

$$\alpha1 = a1 + a2 \cdot f(\Delta A1) + a3 \cdot f(\Delta A2) + a4 \cdot f(\Delta A3) + a5 \cdot f(\Delta A4)$$

$$\alpha2 = b1 + b2 \cdot f(\Delta A1) + b3 \cdot f(\Delta A2) + b4 \cdot f(\Delta A3) + b5 \cdot f(\Delta A4)$$

Here, a5 and b5 are constants. Each of a5 and b5 may be 0 (zero). However, a case where the constants a1 to a5 and the constants b1 to b5 are all 0 at the same time is excluded. $f(\Delta A4)$ is an $n^{th}$-order function of the fourth variation $\Delta A4$ (n: an integer of 1 or greater). The function $f(\Delta A4)$ included in the first correction amount $\alpha1$ and the function $f(\Delta A4)$ included in the second correction amount $\alpha2$ may be the same or different from each other.

In the present example, the third correction amount $\alpha3$ that is used so as to calculate the second blood light absorber concentration $\Phi2$ is expressed by a following equation.

$$\alpha3 = c1 + c2 \cdot f(\Delta A1) + c3 \cdot f(\Delta A2) + c4 \cdot f(\Delta A3) + c5 \cdot f(\Delta A4)$$

Here, c5 is a constant. c5 may be 0 (zero). However, a case where the constants a1 to a5, the constants b1 to b5 and the constant c1 to c5 are all 0 at the same time is excluded. The function $f(\Delta A1)$, the function $f(\Delta A2)$, the function $f(\Delta A3)$, and the function $f(\Delta A4)$ included in the third correction amount $\alpha3$ may be each the same as or different from the function $f(\Delta A1)$, the function $f(\Delta A2)$, the function $f(\Delta A3)$, and the function $f(\Delta A4)$ included in each of the first correction amount $\alpha1$ and the second correction amount $\alpha2$.

In addition, it is possible to individually calculate a third blood light absorber concentration $\Phi3$ (namely, a concentration of a third blood light absorber) by using the fourth light L4. For example, a concentration of oxyhemoglobin, a concentration of deoxyhemoglobin and a concentration of carboxyhemoglobin in the arterial blood can be individually calculated. Specifically, the one or more processors 132 are configured to calculate the third blood light absorber concentration $\Phi3$, based on a ratio of a value obtained by adding a fourth correction amount $\alpha4$ to the fourth variation $\Delta A4$ and a value obtained by adding the first correction amount $\alpha1$ to the first variation $\Delta A1$, a value obtained by adding the second correction amount $\alpha2$ to the second variation $\Delta A2$ or a value obtained by adding the third correction amount $\alpha3$ to the third variation $\Delta A3$. That is, a following equation is presented.

$$\Phi3 = (\Delta A1 + \alpha1)/(\Delta A4 + \alpha4); \text{ or}$$

$$\Phi3 = (\Delta A2 + \alpha2)/(\Delta A4 + \alpha4); \text{ or}$$

$$\Phi3 = (\Delta A3 + \alpha3)/(\Delta A4 + \alpha4); \text{ or}$$

Here, the fourth correction amount $\alpha4$ is expressed by a following equation.

$$\alpha4 = d1 + d2 \cdot f(\Delta A1) + d3 \cdot f(\Delta A2) + d4 \cdot f(\Delta A3) + d5 \cdot f(\Delta A4)$$

Here, d1, d2, d3, d4, and d5 are constants. Each of d1, d2, d3, d4, and d5 may be 0 (zero). However, a case where the constants d1 to d5, the constants a1 to a5, the constants b1 to b5 or the constants c1 to c5 in the equation are all 0 at the same time is excluded. The function $f(\Delta A1)$, the function $f(\Delta A2)$, the function $f(\Delta A3)$, and the function $f(\Delta A4)$ included in the fourth correction amount $\alpha4$ may be each the same as or different from the function $f(\Delta A1)$, the function $f(\Delta A2)$, the function $f(\Delta A3)$, and the function $f(\Delta A4)$ included in each of the first correction amount $\alpha1$, the second correction amount $\alpha2$, and the third correction amount $\alpha3$.

In a case where the constant d2, the constant d3, the constant d4, and the constant d5 are 0, the fourth correction amount $\alpha4$ becomes a constant term. In this case, the constant d1 is an example of the fourth constant.

That is, the fourth wavelength $\lambda4$ is selected as a wavelength that shows a significant difference in the absorbance of the third blood light absorber with respect to the first wavelength $\lambda1$, the second wavelength $\lambda2$ or the third wavelength $\lambda3$. Each constant and each function relating to the fourth variation $\Delta A4$ are statistically determined so as to suppress the effect of the individual difference with respect to the light absorption of the venous blood and tissues, based on test data and clinical data obtained from a plurality of subjects for the third blood light absorber concentration $\Phi3$.

The one or more processors 132 are configured to output a third output signal OS3 corresponding to the third blood light absorber concentration $\Phi 3$ from the output interface 133. The third output signal OS3 is provided to appropriate processing. Examples of the appropriate processing include calculation of a value that can be acquired based on the concentration $\Phi 3$, display of at least one of a value of the concentration $\Phi 3$ and a value acquired based on the concentration $\Phi 3$, a notification operation based on at least one of a value of the concentration $\Phi 3$ and a value acquired based on the concentration $\Phi 3$, and the like.

According to the above configuration, the calculation accuracy of the third blood light absorber concentration $\Phi 3$ can also be enhanced, based on the principle described with respect to the calculation of the first blood light absorber concentration $\Phi 1$.

Note that, in a case where four different wavelengths are used, it is not necessarily required to output calculation results of a plurality of blood light absorber concentrations. In the present example, only one calculation result of the first blood light absorber concentration $\Phi 1$, the second blood light absorber concentration $\Phi 2$, and the third blood light absorber concentration $\Phi 3$ may be output. Also in this case, it is possible to enhance the calculation accuracy of each concentration, as compared to the case where the two wavelengths are used.

As described above, the concentrations of each of the plurality of light absorbers included in the blood not only increase or decrease individually but also influence each other. For example, the increase or decrease in the second blood light absorber concentration $\Phi 2$ and the increase or decrease in the third blood light absorber concentration $\Phi 3$ may affect the increase or decrease in the first blood light absorber concentration $\Phi 1$. The equation for calculating the first blood light absorber concentration $\Phi 1$ by using the first light L1 and the second light L2 includes, in the correction term, the information about the third light L3 that is used so as to calculate the second blood light absorber concentration $\Phi 2$ and the information about the fourth light L4 that is used so as to calculate the third blood light absorber concentration $\Phi 3$. Therefore, when calculating the first blood light absorber concentration $\Phi 1$, the effects of the second blood light absorber concentration $\Phi 2$ and the third blood light absorber concentration $\Phi 3$ can be taken into consideration. Since the number of the blood light absorbers whose effects can be taken into consideration increases, it is possible to further enhance the calculation accuracy of the first blood light absorber concentration $\Phi 1$. The same also applies to the second blood light absorber concentration $\Phi 2$ and the third blood light absorber concentration $\Phi 3$.

As exemplified in FIGURE, the pulse photometry system 10 may include a fifth emitter 115.

The fifth emitter 115 is configured to emit a fifth light L5 including a fifth wavelength $\lambda 5$. The fifth wavelength $\lambda 5$ is different from the first wavelength $\lambda 1$, the second wavelength $\lambda 2$, the third wavelength $\lambda 3$, and the fourth wavelength $\lambda 4$. The fifth emitter 115 may also be configured to include a light-emitting element configured to emit a light including the fifth wavelength $\lambda 5$ or may also be configured so that the light of the fifth wavelength $\lambda 5$ is emitted by enabling a light of a wavelength, which is different from the fifth wavelength $\lambda 5$, emitted from the light-emitting element to pass through an appropriate optical element. Examples of the light-emitting element include a light-emitting diode (LED), a laser diode (LD), an EL element and the like.

In this case, the detector 12 is required to have a light-receiving element having sensitivity to the fifth wavelength $\lambda 5$.

The fifth emitter 115 is configured to be attached to the body 20 of the subject. In the present example, the fifth emitter 115 is arranged so that the fifth light L5 passes through the body 20 and is then incident on the detector 12. The fifth emitter 115 may also be arranged so that the fifth light L5 is reflected on the body 20 and is then incident on the detector 12.

In this case, the one or more processors 132 are configured to cause the fifth emitter 115 to emit the fifth light L5. Specifically, a fifth control signal. CS5 for causing the fifth emitter 115 to emit the fifth light L5 is output from the output interface 133 at a timing different from the first control signal CS1, the second control signal CS2, the third control signal CS3, and the fourth control signal CS4. The fifth control signal CS5 may be an analog signal or a digital signal.

When the fifth light L5 passing through the body 20 is incident on the detector 12, the detector 12 outputs a fifth detection signal DS5 corresponding to an incident intensity of the fifth light L5. The fifth detection signal DS5 is an example of the fifth signal.

The input interface 131 of the pulse photometer 13 is configured to receive the fifth detection signal DS5, in addition to the first detection signal DS1, the second detection signal DS2, the third detection signal DS3, and the fourth detection signal DS4. The one or more processors 132 of the pulse photometer 13 are configured to calculate at least one blood light absorber concentration in the body 20 of the subject, based on the first detection signal DS1, the second detection signal DS2, the third detection signal DS3, the fourth detection signal DS4, and the fifth detection signal DS5.

Same or similarly to the first light L1, the second light L2, the third light L3, and the fourth light L4, an absorbance A5 of the fifth light L5 can also be defined. In addition, a fifth variation $\Delta A5$ corresponding to a variation of the absorbance A5 due to blood pulsation of the subject can be defined.

In the present example, the first correction amount $\alpha 1$ and the second correction amount $\alpha 2$ that are used so as to calculate the first blood light absorber concentration $\Phi 1$ are expressed as follows.

$$\alpha 1 = a1 + a2 \cdot f(\Delta A1) + a3 \cdot f(\Delta A2) + a4 \cdot f(\Delta A3) + a5 \cdot f(\Delta A4) + a6 \cdot f(\Delta A5)$$

$$\alpha 2 = b1 + b2 \cdot f(\Delta A1) + b3 \cdot f(\Delta A2) + b4 \cdot f(\Delta A3) + b5 \cdot f(\Delta A4) + b6 \cdot f(\Delta A5)$$

Here, a6 and b6 are constants. Each of a6 and b6 may be 0 (zero). However, a case where the constants a1 to a6 and the constants b1 to b6 are all 0 at the same time is excluded. $f(\Delta A5)$ is an $n^{th}$-order function of the fifth variation $\Delta A5$ (n: an integer of 1 or greater). The function $f(\Delta A5)$ included in the first correction amount $\alpha 1$ and the function $f(\Delta A5)$ included in the second correction amount $\alpha 2$ may be the same or different from each other.

In the present example, the third correction amount $\alpha 3$ that is used so as to calculate the second blood light absorber concentration $\Phi 2$ is expressed by a following equation.

$$\alpha 3 = c1 + c2 \cdot f(\Delta A1) + c3 \cdot f(\Delta A2) + c4 \cdot f(\Delta A3) + c5 \cdot f(\Delta A4) + c6 \cdot f(\Delta A5)$$

Here, c6 is a constant. c6 may be 0 (zero). However, a case where the constants a1 to a6, the constants b1 to b6 and the constant c1 to c6 are all 0 at the same time is excluded. The function $f(\Delta A1)$, the function $f(\Delta A2)$, the function $f(\Delta A3)$, the function $f(\Delta A4)$, and the function $f(\Delta A5)$ included in the third correction amount $\alpha 3$ may be each the same as or different from the function f($\Delta A1$), the function f($\Delta A2$), the function f($\Delta A3$), the function f($\Delta A4$), and the function f($\Delta A5$) included in each of the first correction amount $\alpha 1$ and the second correction amount $\alpha 2$.

In the present example, a fourth correction amount $\alpha 4$ that is used so as to calculate the third blood light absorber concentration $\Phi 3$ is expressed by a following equation.

$$\alpha 4 = d1 + d2 \cdot f(\Delta A1) + d3 \cdot f(\Delta A2) + d4 \cdot f(\Delta A3) + d5 \cdot f(\Delta A4) + d6 \cdot f(\Delta A5)$$

Here, $d6$ is a constant. $d6$ may be 0 (zero). However, a case where the constants $a1$ to $a6$, the constants $b1$ to $b6$, the constant $c1$ to $c6$ and the constants $d1$ to $d6$ are all 0 at the same time is excluded. The function f($\Delta A1$), the function f($\Delta A2$), the function f($\Delta A3$), the function f($\Delta A4$), and the function f($\Delta A5$) included in the fourth correction amount $\alpha 4$ may be each the same as or different from the function f($\Delta A1$), the function f($\Delta A2$), the function f($\Delta A3$), the function f($\Delta A4$), and the function f($\Delta A5$) included in each of the first correction amount $\alpha 1$, the second correction amount $\alpha 2$, and the third correction amount $\alpha 3$.

In addition, it is possible to individually calculate a fourth blood light absorber concentration $\Phi 4$ (namely, a concentration of a fourth blood light absorber) by using the fifth light L5. For example, a concentration of oxyhemoglobin, a concentration of deoxyhemoglobin, a concentration of carboxyhemoglobin and a concentration of methemoglobin in the arterial blood can be individually calculated. Specifically, the one or more processors 132 are configured to calculate the fourth blood light absorber concentration $\Phi 4$, based on a ratio of a value obtained by adding a fifth correction amount $\alpha 5$ to the fifth variation $\Delta A5$ and a value obtained by adding the first correction amount $\alpha 1$ to the first variation $\Delta A1$, a value obtained by adding the second correction amount $\alpha 2$ to the second variation $\Delta A2$, a value obtained by adding the third correction amount $\alpha 3$ to the third variation $\Delta A3$ or a value obtained by adding the fourth correction amount $\alpha 4$ to the fourth variation $\Delta A4$. That is, a following equation is presented.

$$\Phi 3 = (\Delta A1 + \alpha 1)/(\Delta A5 + \alpha 5); \text{ or}$$

$$\Phi 3 = (\Delta A2 + \alpha 2)/(\Delta A5 + \alpha 5); \text{ or}$$

$$\Phi 3 = (\Delta A3 + \alpha 3)/(\Delta A5 + \alpha 5); \text{ or}$$

$$\Phi 3 = (\Delta A4 + \alpha 4)/(\Delta A5 + \alpha 5)$$

Here, the fifth correction amount $\alpha 5$ is expressed by a following equation.

$$\alpha 5 = e1 + e2 \cdot f(\Delta A1) + e3 \cdot f(\Delta A2) + e4 \cdot f(\Delta A3) + e5 \cdot f(\Delta A4) + e6 \cdot f(\Delta A5)$$

Here, $e1$, $e2$, $e3$, $e4$, $e5$, and $e6$ are constants. Each of $e1$, $e2$, $e3$, $e4$, $e5$, and $e6$ may be 0 (zero). However, a case where the constants $e1$ to $e6$, the constants $a1$ to $a6$, the constants $b1$ to $b6$, the constants $c1$ to $c6$ or the constants $d1$ to $d6$ in the equation are all 0 at the same time is excluded. The function f($\Delta A1$), the function f($\Delta A2$), the function f($\Delta A3$), the function f($\Delta A4$), and the function f($\Delta A5$) included in the fifth correction amount $\alpha 5$ may be each the same as or different from the function f($\Delta A1$), the function f($\Delta A2$), the function f($\Delta A3$), the function f($\Delta A4$), and the function f($\Delta A5$) included in each of the first correction amount $\alpha 1$, the second correction amount $\alpha 2$, the third correction amount $\alpha 3$, and the fourth correction amount $\alpha 4$.

In a case where the constant $e2$, the constant $e3$, the constant $e4$, the constant $e5$, and the constant $e6$ are 0, the fifth correction amount $\alpha 5$ becomes a constant term. In this case, the constant $e1$ is an example of the fifth constant.

That is, the fifth wavelength $\lambda 5$ is selected as a wavelength that shows a significant difference in the absorbance of the fourth blood light absorber with respect to the first wavelength $\lambda 1$, the second wavelength $\lambda 2$, the third wavelength $\lambda 3$, or the fourth wavelength $\lambda 4$. Each constant and each function relating to the fifth variation $\Delta A5$ are statistically determined so as to suppress the effect of the individual difference with respect to the light absorption of the venous blood and tissues, based on test data and clinical data obtained from a plurality of subjects for the fourth blood light absorber concentration $\Phi 4$.

The one or more processors 132 are configured to output a fourth output signal OS4 corresponding to the fourth blood light absorber concentration $\Phi 4$ from the output interface 133. The fourth output signal OS4 is provided to appropriate processing. Examples of the appropriate processing include calculation of a value that can be acquired based on the concentration $\Phi 4$, display of at least one of a value of the concentration $\Phi 4$ and a value acquired based on the concentration $\Phi 4$, a notification operation based on at least one of a value of the concentration $\Phi 4$ and a value acquired based on the concentration $\Phi 4$, and the like.

According to the above configuration, the calculation accuracy of the fourth blood light absorber concentration $\Phi 4$ can also be enhanced, based on the principle described with respect to the calculation of the first blood light absorber concentration $\Phi 1$.

Note that, in a case where five different wavelengths are used, it is not necessarily required to output calculation results of a plurality of blood light absorber concentrations. In the present example, only one calculation result of the first blood light absorber concentration $\Phi 1$, the second blood light absorber concentration $\Phi 2$, the third blood light absorber concentration $\Phi 3$, and the fourth blood light absorber concentration $\Phi 4$ may be output. Also in this case, it is possible to enhance the calculation accuracy of each concentration, as compared to the case where the two wavelengths are used.

As described above, the concentrations of each of the plurality of light absorbers included in the blood not only increase or decrease individually but also influence each other. For example, the increase or decrease in the second blood light absorber concentration $\Phi 2$, the increase or decrease in the third blood light absorber concentration $\Phi 3$ and the increase or decrease in the fourth blood light absorber concentration $\Phi 4$ may affect the increase or decrease in the first blood light absorber concentration $\Phi 1$. The equation for calculating the first blood light absorber concentration $\Phi 1$ by using the first light L1 and the second light L2 includes, in the correction term, the information about the third light L3 that is used so as to calculate the second blood light absorber concentration $\Phi 2$, the information about the fourth light L4 that is used so as to calculate the third blood light absorber concentration $\Phi 3$, and the information about the fifth light L5 that is used so as to calculate the fourth blood light absorber concentration $\Phi 4$. Therefore, when calculating the first blood light absorber concentration $\Phi 1$, the effects of the second blood light absorber concentration $\Phi 2$, the third blood light absorber concentration $\Phi 3$ and the fourth blood light absorber concentration $\Phi 4$ can be taken into consideration. Since the number of the blood light absorbers whose effects can be taken into consideration increases, it is possible to further enhance the calculation accuracy of the first blood light absorber concentration $\Phi 1$. The same also applies to the second blood light absorber concentration Φ2, the third blood light absorber concentration Φ3, and the fourth blood light absorber concentration Φ4.

The one or more processors 132 having the function as described above may be implemented by one or more general-purpose microprocessors configured to operate in cooperation with one or more general-purpose memories. As the one or more general-purpose microprocessors, a CPU, an MPU and a GPU may be exemplified. As the one or more general-purpose memories, a ROM and a RAM may be exemplified. In this case, a computer program configured to execute the above-described processing may be stored in the ROM. The ROM is an example of the storage medium in which the computer program is stored. The one or more general-purpose microprocessors are configured to designate at least a part of the computer program stored on the ROM and to develop the same on the RAM, thereby executing the above-described processing in cooperation with the RAM. The computer program may be pre-installed in the one or more general-purpose memories or may be downloaded from an external server via a communication network and installed in the one or more general-purpose memories. In this case, the external server is an example of the storage medium in which the computer program is stored.

The one or more processors 132 may also be implemented by a dedicated integrated circuit such as a microcontroller, an ASIC, an FPGA and the like capable of executing the computer program. In this case, the computer program is pre-installed in a storage device included in the dedicated integrated circuit. The storage device is an example of the storage medium in which the computer program is stored. The one or more processors 132 may also be implemented by a combination of one or more general-purpose microprocessor and a dedicated integrated circuit.

The embodiment is just exemplary for easy understanding of the presently disclosed subject matter. The configurations of the embodiment can be appropriately changed and improved without departing from the gist of the presently disclosed subject matter.

The pulse photometry system 10 may have a configuration where six or more different wavelengths are used, according to the number and types of the blood light absorbers for which it is required to calculate the concentrations. Other examples of the blood light absorber include bilirubin and glucose.

Examples of the blood light absorber whose concentration is to be calculated include materials that are generated in the body of the subject, and pigments that are injected into the blood vessel for contrast examination and the like.

The invention claimed is:

1. A pulse photometer comprising:
an input interface configured to receive a first signal, which corresponds to an intensity of a first light including a first wavelength passing through a body of a subject, and a second signal, which corresponds to an intensity of a second light including a second wavelength passing through the body; and
one or more processors configured to calculate a concentration of at least one blood light absorber in the subject, based on the first signal and the second signal, wherein the one or more processors are configured to:
acquire a first variation corresponding to a variation of the first light due to blood pulsation in the subject,
acquire a second variation corresponding to a variation of the second light due to the pulsation, and
calculate the concentration of the at least one blood light absorber, based on a value obtained by dividing the first variation by the second variation,
wherein a correction amount is added to at least one of the first variation and the second variation,
wherein the correction amount is based on at least one of a function of the first variation and a function of the second variation, when the correction amount is added to the first variation, and
wherein the correction amount is based on at least one of a first constant, the function of the first variation and the function of the second variation, when the correction amount is added to the second variation.

2. The pulse photometer according to claim 1, wherein the input interface is configured to receive a third signal, which corresponds to an intensity of a third light including a third wavelength passing through the body,
wherein the one or more processors are configured to calculate the concentration of the at least one blood light absorber, based on the first signal, the second signal and the third signal,
wherein the one or more processors are configured to acquire a third variation corresponding to a variation of the third light due to the blood pulsation,
wherein the correction amount is based on at least one of the function of the first variation, the function of the second variation and a function of the third variation, when the correction amount is added to the first variation, and
wherein the correction amount is based on at least one of the first constant, the function of the first variation, the function of the second variation and the function of the third variation, when the correction amount is added to the second variation.

3. The pulse photometer according to claim 2, wherein the input interface is configured to receive a fourth signal, which corresponds to an intensity of a fourth light including a fourth wavelength passing through the body,
wherein the one or more processors are configured to calculate the concentration of the at least one blood light absorber, based on the first signal, the second signal, the third signal and the fourth signal,
wherein the one or more processors are configured to acquire a fourth variation corresponding to a variation of the fourth light due to the blood pulsation,
wherein the correction amount is based on at least one of the function of the first variation, the function of the second variation, the function of the third variation, and a function of the fourth variation, when the correction amount is added to the first variation, and
wherein the correction amount is based on at least one of the first constant, the function of the first variation, the function of the second variation, the function of the third variation, and the function of the fourth variation, when the correction amount is added to the second variation.

4. The pulse photometer according to claim 3, wherein the input interface is configured to receive a fifth signal, which corresponds to an intensity of a fifth light including a fifth wavelength passing through the body,
wherein the one or more processors are configured to calculate the concentration of the at least one blood light absorber, based on the first signal, the second signal, the third signal, the fourth signal and the fifth signal, wherein the one or more processors are configured to acquire a fifth variation corresponding to a variation of the fifth light due to the blood pulsation, wherein the correction amount is based on at least one of the function of the first variation, the function of the second variation, the function of the third variation, the function of the fourth variation and a function of the fifth variation, when the correction amount is added to the first variation, and wherein the correction amount is based on at least one of the first constant, the function of the first variation, the function of the second variation, the function of the third variation, the function of the fourth variation and the function of the fifth variation, when the correction amount is added to the second variation.

5. The pulse photometer according to claim 1, wherein the input interface is configured to receive a third signal, which corresponds to an intensity of a third light including a third wavelength passing through the body, wherein the at least one blood light absorber comprises a first blood light absorber and a second blood light absorber, wherein the one or more processors are configured to acquire a third variation corresponding to a variation of the third light due to the blood pulsation, wherein the one or more processors are configured to calculate a concentration of the first blood light absorber, based on a value obtained by adding the correction amount to the first variation and the value obtained by adding the correction amount to the second variation, wherein the one or more processors are configured to calculate a concentration of the second blood light absorber, based on a value obtained by adding the correction amount to the third variation and the value obtained by adding the correction amount to the first variation or the value obtained by adding the correction amount to the second variation, and wherein the correction amount is based on at least one of a second constant, the function of the first variation, the function of the second variation and a function of the third variation, when the correction amount is added to the third variation.

6. The pulse photometer according to claim 5, wherein the input interface is configured to receive a fourth signal, which corresponds to an intensity of a fourth light including a fourth wavelength passing through the body, wherein the at least one blood light absorber comprises a third blood light absorber, wherein the one or more processors are configured to acquire a fourth variation corresponding to a variation of the fourth light due to the blood pulsation, wherein the one or more processors are configured to calculate a concentration of the third blood light absorber, based on a value obtained by adding the correction amount to the fourth variation, and the value obtained by adding the correction amount to the first variation, the value obtained by adding the correction amount to the second variation or the value obtained by adding the correction amount to the third variation, and wherein the correction amount is based on at least one of a third constant, the function of the first variation, the function of the second variation, the function of the third variation and a function of the fourth variation, when the correction amount is added to the fourth variation.

7. The pulse photometer according to claim 6, wherein the input interface is configured to receive a fifth signal, which corresponds to an intensity of a fifth light including a fifth wavelength passing through the body, wherein the at least one blood light absorber comprises a fourth blood light absorber, wherein the one or more processors are configured to acquire a fifth variation corresponding to a variation of the fifth light due to the blood pulsation, wherein the one or more processors are configured to calculate a concentration of the fourth blood light absorber, based on a value obtained by adding the correction amount to the fifth variation, and the value obtained by adding the correction amount to the first variation, the value obtained by adding the correction amount to the second variation, the value obtained by adding the correction amount to the third variation or a value obtained by adding the correction amount to the fourth variation, and wherein the correction amount is based on at least one of a fourth constant, the function of the first variation, the function of the second variation, the function of the third variation, the function of the fourth variation and a function of the fifth variation, when the correction amount is added to the fifth variation.

8. The pulse photometer according to claim 1, wherein the at least one blood light absorber is at least one of oxyhemoglobin, deoxyhemoglobin, carboxyhemoglobin, and methemoglobin.

9. A pulse photometry system comprising:
a first emitter configured to emit a first light including a first wavelength;
a second emitter configured to emit a second light including a second wavelength;
a detector configured to output a first signal, which corresponds to an intensity of the first light passing through a body of a subject, and a second signal, which corresponds to an intensity of the second light passing through the body; and
one or more processors configured to calculate a concentration of at least one blood light absorber in the subject, based on the first signal and the second signal,
wherein the one or more processors are configured to:
acquire a first variation corresponding to a variation of the first light due to blood pulsation in the subject,
acquire a second variation corresponding to a variation of the second light due to the pulsation, and
calculate the concentration of the at least one blood light absorber, based on a value obtained by dividing the first variation by the second variation,
wherein a correction amount is added to at least one of the first variation and the second variation,
wherein the correction amount is based on at least one of a function of the first variation and a function of the second variation, when the correction amount is added to the first variation, and
wherein the correction amount is based on at least one of a first constant, the function of the first variation and the function of the second variation, when the correction amount is added to the second variation.

10. A non-transitory computer-readable medium storing a computer program capable of being executed by one or more processors of a pulse photometer,
when executed, the computer program causing the pulse photometer to:

receive a first signal, which corresponds to an intensity of a first light including a first wavelength passing through a body of a subject;
receive a second signal, which corresponds to an intensity of a second light including a second wavelength passing through the body;
acquire a first variation corresponding to a variation of the first light due to blood pulsation in the subject,
acquire a second variation corresponding to a variation of the second light due to the pulsation, and
calculate the concentration of the at least one blood light absorber in the subject, based on a value obtained by dividing the first variation by the second variation,
wherein a correction amount is added to at least one of the first variation and the second variation,
wherein the correction amount is based on at least one of a function of the first variation and a function of the second variation, when the correction amount is added to the first variation, and
wherein the correction amount is based on at least one of a first constant, the function of the first variation and the function of the second variation, when the correction amount is added to the second variation.

* * * * *